United States Patent
Hoomani et al.

(10) Patent No.: US 10,254,841 B2
(45) Date of Patent: Apr. 9, 2019

(54) SYSTEM AND METHOD FOR REAL-TIME AGE PROFILING

(71) Applicant: Disney Enterprises, Inc., Burbank, CA (US)

(72) Inventors: Cyrus Hoomani, Studio City, CA (US); Steven Makofsky, Sammamish, WA (US)

(73) Assignee: Disney Enterprises, Inc., Burbank, CA (US)

( * ) Notice: Subject to any disclaimer, the term of this patent is extended or adjusted under 35 U.S.C. 154(b) by 106 days.

(21) Appl. No.: 14/250,289

(22) Filed: Apr. 10, 2014

(65) Prior Publication Data
US 2015/0293594 A1 Oct. 15, 2015

(51) Int. Cl.
| | |
|---|---|
| *G06F 3/01* | (2006.01) |
| *G06F 3/041* | (2006.01) |
| *A61B 5/00* | (2006.01) |
| *G06F 3/0346* | (2013.01) |
| *A61B 5/11* | (2006.01) |
| *A61B 5/117* | (2016.01) |
| *A61B 5/16* | (2006.01) |
| *A61B 5/22* | (2006.01) |
| *G06F 1/16* | (2006.01) |
| *H04L 29/06* | (2006.01) |
| *G06Q 30/02* | (2012.01) |

(52) U.S. Cl.
CPC ............ *G06F 3/017* (2013.01); *A61B 5/117* (2013.01); *A61B 5/1118* (2013.01); *A61B 5/1124* (2013.01); *A61B 5/1125* (2013.01); *A61B 5/162* (2013.01); *A61B 5/225* (2013.01); *A61B 5/681* (2013.01); *A61B 5/6898* (2013.01); *G06F 1/163* (2013.01); *G06F 1/1626* (2013.01); *G06F 1/1684* (2013.01); *G06F 1/1694* (2013.01); *G06F 3/014* (2013.01); *G06F 3/0346* (2013.01); *G06F 3/0412* (2013.01); *G06Q 30/0251* (2013.01); *H04L 63/102* (2013.01); *G06F 2203/04105* (2013.01)

(58) Field of Classification Search
CPC ......... G06F 3/017; G06F 3/011; G06F 19/34; G06F 1/1626; G06F 1/163; G06F 1/1684; G06F 1/1694; G06F 2203/04105; G06F 3/014; G06F 3/0346; G06F 3/0412; G06F 3/0414; H04L 63/102; G06Q 30/0251
USPC ............ 345/156–173, 168; 348/77; 715/863
See application file for complete search history.

(56) References Cited

U.S. PATENT DOCUMENTS

| | | | |
|---|---|---|---|
| 2009/0118593 A1* | 5/2009 | Jung | ............... G06Q 50/22 600/300 |
| 2010/0042564 A1* | 2/2010 | Harrison | ................ G06F 3/01 706/13 |

(Continued)

*Primary Examiner* — Hong Zhou
(74) *Attorney, Agent, or Firm* — Farjami & Farjami LLP

(57) ABSTRACT

There are provided systems and methods for real-time age profiling. One system includes at least one sensor, a memory storing an algorithm, and a processor configured to execute the algorithm to receive data corresponding to a user interaction with the at least one sensor and calculate an age of a user using the data corresponding to the user interaction. The data corresponding to the user interaction may include pressure data from a pressure sensor, orientation data from an orientation sensor, motion data from a motion sensor, or interaction data from an interaction sensor.

16 Claims, 6 Drawing Sheets

(56) References Cited

U.S. PATENT DOCUMENTS

| | | | | |
|---|---|---|---|---|
| 2011/0102570 A1* | 5/2011 | Wilf | ............... | G06F 3/017 |
| | | | | 348/77 |
| 2011/0307260 A1* | 12/2011 | Zhang | ............... | G06F 3/017 |
| | | | | 704/275 |
| 2013/0083007 A1* | 4/2013 | Geisner | ............... | G06T 19/006 |
| | | | | 345/419 |
| 2013/0285921 A1* | 10/2013 | Alberth, Jr. | ............... | G06F 1/1652 |
| | | | | 345/173 |
| 2014/0125620 A1* | 5/2014 | Panther | ............... | G06F 3/011 |
| | | | | 345/173 |
| 2014/0191974 A1* | 7/2014 | Sako | ............... | G06K 9/00288 |
| | | | | 345/168 |
| 2014/0210728 A1* | 7/2014 | Busse | ............... | G06F 9/4443 |
| | | | | 345/173 |
| 2014/0278747 A1* | 9/2014 | Gumm | ............... | G06Q 30/0201 |
| | | | | 705/7.29 |
| 2014/0327619 A1* | 11/2014 | Chang | ............... | G06F 3/03543 |
| | | | | 345/163 |
| 2015/0120202 A1* | 4/2015 | Armstrong | ............... | A61B 5/1118 |
| | | | | 702/19 |

* cited by examiner

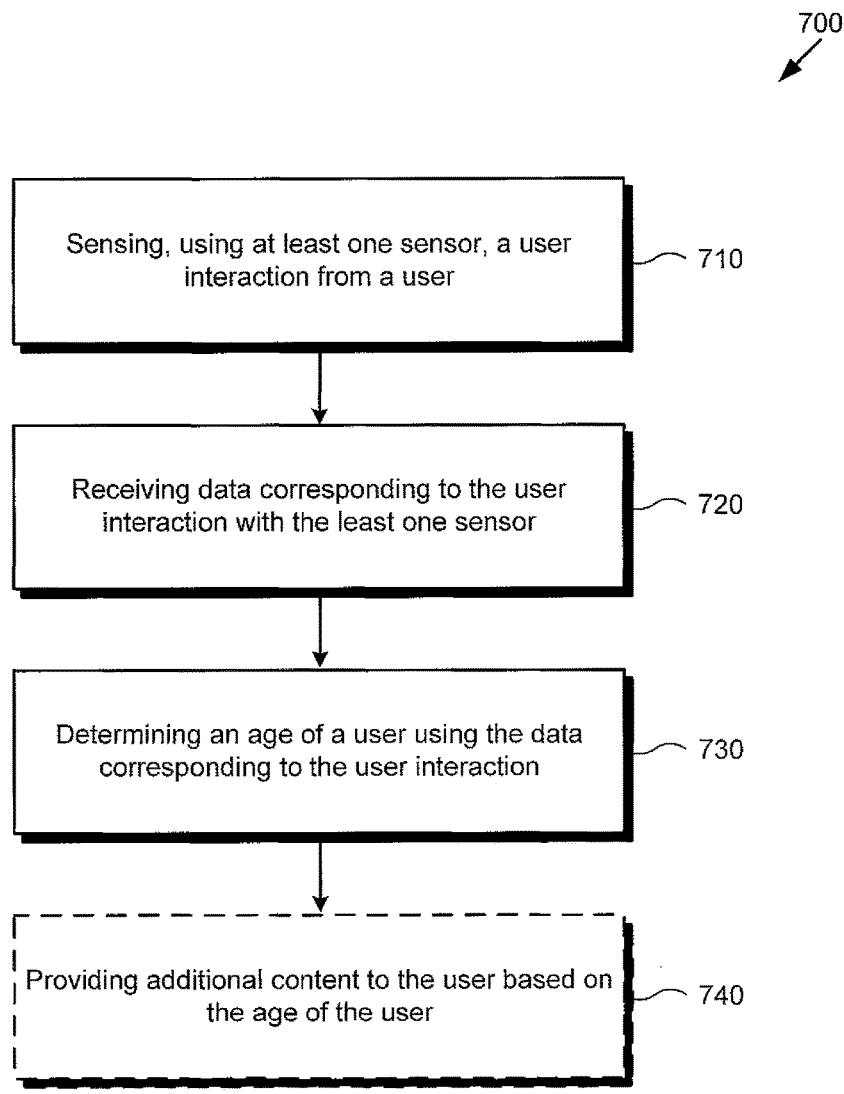

SYSTEM AND METHOD FOR REAL-TIME AGE PROFILING

BACKGROUND

Determining the age of a user of an electronic device can be important when deciding which types of content are appropriate for the user and thus, should be provided to the user. For example, certain websites that can be accessed using the electronic device, or applications that can be loaded on the electronic device, may only be appropriate for adults. As another example, when businesses pay for advertisements to be displayed on the electronic device, it is important for the businesses to target their advertisements towards specific age groups.

One method of solving the problem of determining the age of the user is for websites and applications to ask the user to input his or her age. However, this method of determining the age of a user has many flaws. Specifically, when asking the user to input his or her age, the user may not be truthful. Furthermore, asking the user to input his or her age may require the user to input personal information that the user may not wish to disclose or input false information.

SUMMARY

The present disclosure is directed to systems and methods for real-time age profiling, substantially as shown in and/or described in connection with at least one of the figures, as set forth more completely in the claims.

BRIEF DESCRIPTION OF THE DRAWINGS

FIG. 7 shows a flowchart illustrating a method for real-time age profiling, according to one implementation of the present disclosure.

DETAILED DESCRIPTION

Figure 1:
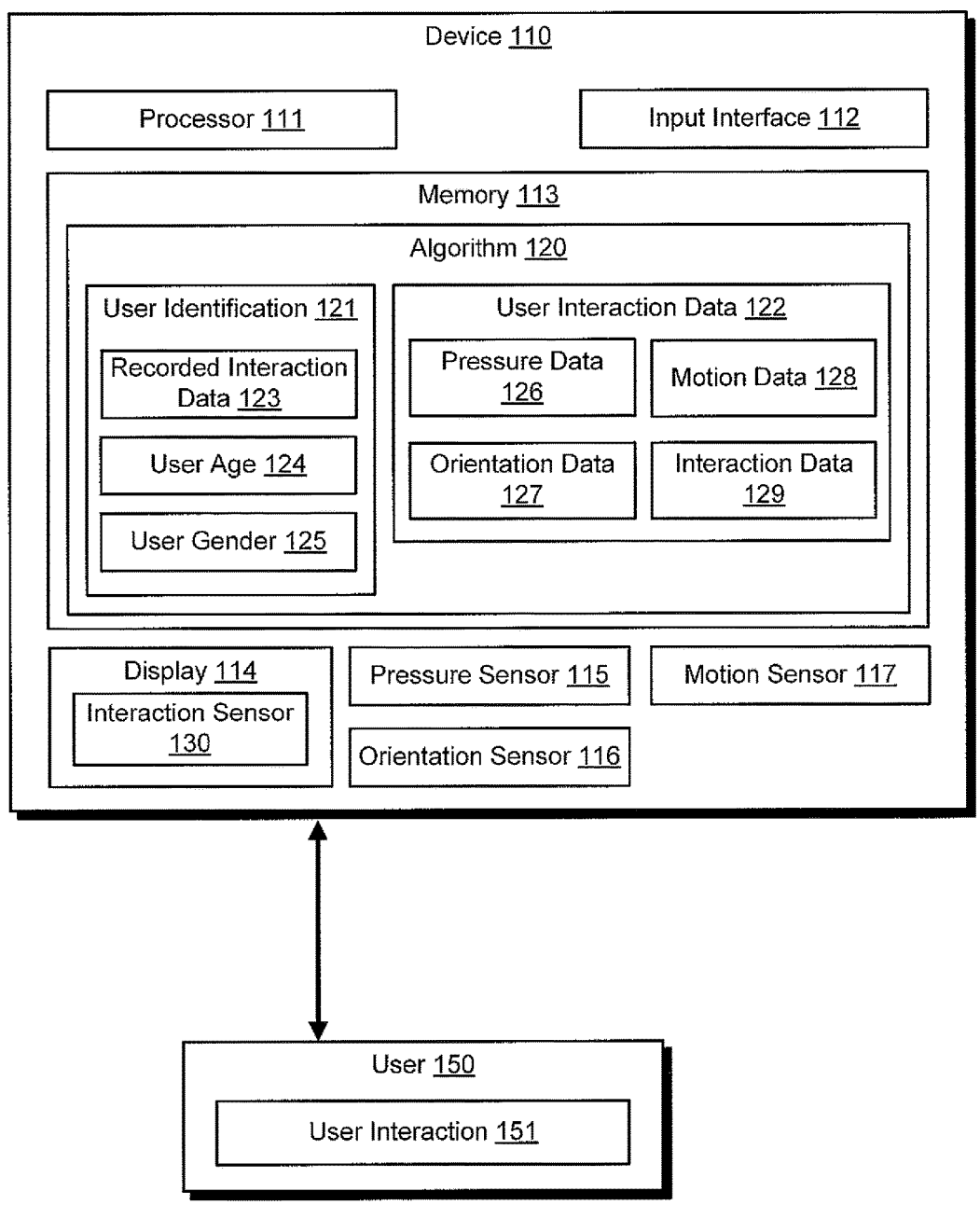
FIG. 1 presents a system for real-time age profiling, according to one implementation of the present disclosure.

The following description contains specific information pertaining to implementations in the present disclosure. The drawings in the present application and their accompanying detailed description are directed to merely exemplary implementations. Unless noted otherwise, like or corresponding elements among the figures may be indicated by like or corresponding reference numerals. Moreover, the drawings and illustrations in the present application are generally not to scale, and are not intended to correspond to actual relative dimensions.

FIG. 1 presents a system for real-time age profiling, according to one implementation of the present disclosure. System 100 of FIG. 1 includes device 110 and user 150. Device 110 includes processor 111, input interface 112, memory 113, display 114, pressure sensor 115, orientation sensor 116, and motion sensor 117. Memory 113 includes algorithm 120. Display 114 includes interaction sensor 130. Algorithm 120 includes user identification 121 and user interaction data 122. User identification 121 includes recorded interaction data 123, user age 124, and user gender 125. User interaction data 122 includes pressure data 126, orientation data 127, motion data 128, and interaction data 129. User 150 includes user interaction 151.

Device 110 may comprise a personal computer, a mobile phone, a tablet, a video game console, a wearable device such as a watch, or any other device capable of executing algorithm 120 in memory 113. As shown in FIG. 1, device 110 includes input interface 112 and display 114. Input interface 112 may comprise, for example, a keyboard, a mouse, a game controller, a touch-screen input, a thermal and/or electrical sensor, or any other device capable of accepting user input for use with device 110. Display 114 may comprise a liquid crystal display (LCD) screen built into device 110. In alternative implementations of the present disclosure, display 114 may be another type of display hardware, such as cathode-ray tubes (CRT) monitors. In yet other implementations, display 114 may also be touch sensitive and may serve as input interface 112. Moreover, input interface 112 and display 114 may be externally attached to device 110 through physical or wireless connection.

Device 110 further includes processor 111 and memory 113. Processor 111 may be configured to access memory 113 to store received input or to execute commands, processes, or programs stored in memory 113, such as algorithm 120. Processor 111 may correspond to a processing device, such as a microprocessor or similar hardware processing device, or a plurality of hardware devices. However, in other implementations, processor 111 refers to a general processor capable of performing the functions required of device 110. Memory 113 is capable of storing commands, processes, and programs for execution by processor 111. Memory 113 may be instituted as ROM, RAM, flash memory, or any sufficient memory capable of storing a set of commands. In other implementations, memory 113 may correspond to a plurality memory types or modules.

As illustrated in FIG. 1, device 110 further includes four different hardware sensors, pressure sensor 115, orientation sensor 116, motion sensor 117, and interaction sensor 130. Device 110 utilizes the hardware sensors to collect data corresponding to a user's interaction with device 110, such as user interaction 151 from user 150 with device 110. User interaction 151 includes any interaction user 150 makes with device 110 while user 150 is utilizing device 110. For example, user interaction 151 can include, but is not limited to, user 150 picking device 110 up, user 150 moving device 110, user 150 holding device 110, or user 150 utilizing the buttons and functions of device 110. As such, data corresponding to user interaction 151 may include how much pressure user 150 applies to device 110, the orientation of how user 150 holds device, how user 150 moves device 110, how user 150 interacts with the buttons and functions of device, or any other data that can be collected regarding user interaction 151 with device 110.

As such, pressure sensor 115 is utilized by device 110 to sense both the amount of pressure user 150 applies to device 110 and where user 150 applies that pressure on device 110 during user interaction 151. As will be illustrated more with regards to FIG. 2, pressure sensor 115 can sense pressure on all parts of device 110. For example, pressure sensor 115 may collect data corresponding how much pressure user 150 applies to display 114 of device 110 while user 150 is pressing different buttons displayed on display 114. For a second example, pressure sensor 115 may collect data corresponding how much pressure user 150 applies to the back of device 110 when user 150 is holding device 110 in his or her hands. Finally, for a third example, pressure sensor 115 may collect data corresponding to how much pressure is applied to the sides of device 110 while user 150 is griping device 110 in his her or hands. By collecting pressure data 126, which corresponds to the data collected by pressure sensor 115 during user interaction 151, algorithm 120 can utilize pressure data 126 to determine the age of user 150.

Orientation sensor 116 is utilized by device 110 to sense the orientation device 110 during user interaction 151. As will be illustrated more with regards to FIG. 3, orientation sensor 116 can sense any orientation that device 110 is used in. For example, orientation sensor 116 may collect data that includes device 110 is being used in an upward position, where an upward position means that display 114 is facing upwards. For a second example, orientation sensor 116 may collect data that includes device 110 is being used in a backwards position, where a backwards position means display 114 is facing downwards. Finally, for a third example, orientation sensor 116 may collect data that includes device 110 is being used in a horizontal position, where a horizontal position means that display 114 horizontal to the ground. By collecting orientation data 127, which corresponds to the data collected by orientation sensor 116 during user interaction 151, algorithm 120 can utilize orientation data 127 to determine the age of user 150.

Motion sensor 117 is utilized by device 110 to sense the movement of device 110 during user interaction 151. As will be illustrated more with regards to FIG. 4, motion sensor 117 can sense any movement that device 110 makes while user 150 interacts with device 110. For example, motion sensor 117 may collect data that device 110 was lifted up in the air or brought down close to the ground. For a second example, motion sensor 117 may collect data that device 110 was moved to the left or right, or was spun around. Furthermore, motion sensor 117 may also collect data on how fast device 110 was moved. By collecting motion data 128, which corresponds to the data collected by motion sensor 117 during user interaction 151, algorithm 120 can utilize motion data 128 to determine the age of user 150.

Finally, interaction sensor 130 senses a user's interaction with display 114 during user interaction 151. For example, and as discussed above, in one implementation, display 114 may also be touch sensitive and may serve as input interface 112. In such an implementation, interaction sensor 130 may collect data corresponding to how many times user 150 taps on display 114, how many of the buttons on display 114 user 150 pressed during a predetermined time, or how many times user 150 pressed the buttons on display 114 during the predetermined times. Furthermore, as will be illustrated more with regards to FIG. 5, interaction sensor 130 may collect data corresponding to the dimensions of a hand of user 150, such as how big the hand of user 150 is or how far apart the fingers are spaced on the hand of user 150. By collecting interaction data 129, which corresponds to the data collected by interaction sensor 130 during user interaction 151, algorithm 120 can utilize interaction data 129 to determine the age of user 150.

It should be noted that the implementation of FIG. 1 illustrates display 114 including interaction sensor 130, however, the present disclosure is not limited to display 114 including interaction sensor 130. For example, in one implementation where display 114 is not touch sensitive and does not include input interface 112, input interface 112 includes interaction sensor 130. In such an implementation, input interface 112 would include a number of buttons. Interaction sensor 130 would thus collect data corresponding to how many of the buttons on user interface 112 user 150 pressed during a predefined time, and how many times user 150 pressed the buttons on user interface 112 during the predefined time. For another example, in another implementation, both user interface 112 and display 114 would include interaction sensors that collect data corresponding to user interactions with both user interface 112 and display 114.

It should further be noted that in the implementation of FIG. 1, device 110 includes four separate sensors, pressure sensor 115, orientation sensor 116, motion sensor 117, and interaction sensor 130, however, the present disclosure is not limited to the implementation of FIG. 1. In other implementations, device 110 may include more or less than four sensors for sensing user interactions. Furthermore, in other implementations, at least two of the four sensors may be combined into a single sensor. For example, orientation sensor 116 and motion sensor 117 may be combined into a single hardware sensor that performs the functions and collects the data from each of orientation sensor 116 and motion sensor 117.

Also illustrated in FIG. 1, device 110 includes algorithm 120. Device 110 utilizes algorithm 120 to determine the age of the user of device 110, such as user age 124 of user 150 of device 110. Algorithm 120 calculates user age 124 using user identification 121 based on user interaction data 122, where user interaction data 122 includes pressure data 126, orientation data 127, motion data 128, and interaction data 129. As discussed above, pressure data 126 corresponds to the pressure data collected by pressure sensor 115, orientation data 127 corresponds to the orientation data collected by orientation sensor 116, motion data 128 corresponds to the motion data collected by motion sensor 117, and interaction data 129 corresponds to the data collected by interaction sensor 130, all of which were described in detail above.

User identification 121 calculates user age 124 of users based on user interaction data 122 by comparing user interaction data 122 with recorded interaction data 123. Recorded interaction data 123 includes data describing how users of device 110 are known to interact with device 110 based on their age. For example, recorded interaction data 123 may specify that people over the age of thirteen tend to slowly press buttons on display 114 while people over the age of thirteen tend to rapidly press buttons on display 114. In such an example, if interaction data 129 specifies that user 150 rapidly pressed multiple buttons on display 114, then user identification 121 would calculate that user 150 is under the age of thirteen. For another example, recorded interaction data 123 may specify that people over the age of thirteen tend to use device 110 while device 110 is facing upwards while people under the age of thirteen tend to use device 110 while device 110 is facing downwards. In such an example, if orientation data 127 specifies that user 150 mostly uses device 110 while device 110 is facing downwards, then user identification 121 would calculate that user 150 is under the age of thirteen.

It should be noted that the examples above only discuss using one type of interaction data from user interaction data 122 to calculate user age 124 using user identification 121, however, the present disclosure is not limited to only using one type of interaction data 122. For example, user identification 121 may compare two or more of pressure data 126, orientation data 127, motion data 128, and interaction data 129 against recorded interaction data 123 to calculate user age 124. Furthermore, if more than one type of user interaction data 122 is used to calculate user age 124, then user identification 121 may give weights to each type of user interaction. For example, if user identification 121 is using orientation data 127 and motion data 128 to calculate user age 124 of user 150, user identification 121 may give more weight to motion data 128 in calculating user age 124 if motion data 128 gives a better idea of user age 124.

It should further be noted that the examples above discuss algorithm 120 determining a range for user age 124, such as older or younger than thirteen years old, however, the present disclosure is not limited to the examples above. In one implementation, algorithm 120 will calculate the exact age of a user for user age 124. For example, algorithm 120 will calculate that user age 124 of user 150 is ten years old. However, as discussed above, in other implementations, algorithm 120 will calculate a range of ages for a user. For example, algorithm 120 will specify that user age 124 of user 150 is below thirteen years old. For another example, algorithm 120 will specify that user age 124 of user 150 is between thirteen years old and eighteen years old.

Also illustrated in FIG. 1, user identification 121 includes user gender 125. User identification 121 may calculate the gender of a user of device 110 in a similar way as user identification 121 calculated user age 124. For example, user identification 121 may compare user interaction data 122 with recorded interaction data 123, where recorded interaction data 123 further includes data describing how users of device 110 are known to interact with device 110 based on their gender. In such an example, user identification 121 would calculate whether user gender 125 is male or female based on the comparing of user interaction data 122 with recorded interaction data 123.

In the implementation of FIG. 1, user 150 interacts with device 110 through user interaction 151. During user interaction 151, device 110 executes algorithm 120 to receive pressure data 126, orientation data 127, motion data 128, and interaction data 129 from pressure sensor 115, orientation sensor 116, motion sensor 117, and interaction sensor 130, respectively. Algorithm 120 then calculates user age 124 based on user interaction data 122 using user identification 121, where user identification 121 compares user interaction data 122 to recorded interaction data 123 to compute user age 124. Furthermore, algorithm 120 may also calculate user gender 125 based on user interaction data 122 also using user identification 121, where user identification 121 again compares user interaction data 122 with recorded interaction data 123 to compute user gender 125.

It should be noted that in the implementation of FIG. 1, algorithm 120 may start collecting user interaction data 122 after a specific event has occurred between device 110 and user 150. Events can include any type of interaction user 150 has with device 110. For example, algorithm 120 may start collecting user interaction data 122 right after device 110 first senses an interaction between user 150 and device 110, such as when user 150 picks device 110 up. For a second example, algorithm 120 may start collecting interaction data 122 right after user 150 unlocks device 110. Finally, for a third example, algorithm 120 may start collecting interaction data 122 when device 110 loads a website or application that requires the age of user 150.

It should further be noted that after device 110 computes user age 124 and user gender 125, device 110 may provide additional content to user 150 based on user age 124 and user gender 125. Additional content can include, but is not limited to, targeted advertisements, websites, or games. For example, device 110 may load and display targeted advertisements on display 114 to user 150 based on user age 124 or user gender 125. In such an example, device 110 may display a toy advertisement on display 114 if user age 124 is determined to be around thirteen years old. Furthermore, again in such an example, device 110 may display a dress advertisement on display 114 if user gender 125 is determined to be a female.

Finally, it should be noted that the implementation of FIG. 1 illustrates algorithm 120 stored in memory 113 of user device 110 and being automatically executed by user device 110 to determine user age 124 and user gender 125, however, the present disclosure is not limited to the implementation of FIG. 1. For example, in one implementation, algorithm 120 may be a software algorithm in the operating system, or may be a software application that user 150 of user device 110 downloads on user device 110. In such an implementation, processor 111 of user device 110 would activate the software application to determine the age and gender of user 150 in a similar way as algorithm 120 determines user age 124 and user gender 125.

Figure 2:
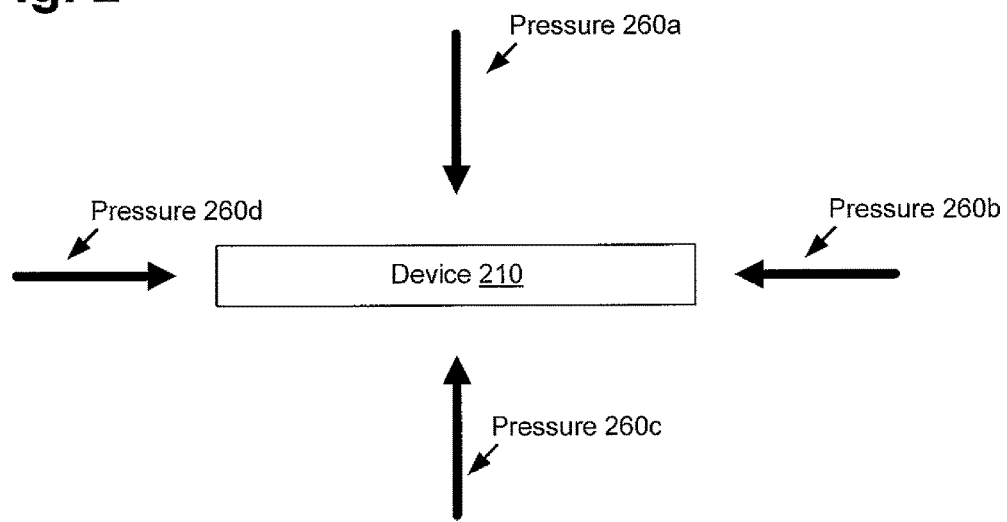
FIG. 2 presents an example of detecting pressure on a device by using a pressure sensor, according to one implementation of the present disclosure.

FIG. 2 presents an example of detecting pressure on a device by using a pressure sensor, according to one implementation of the present disclosure. FIG. 2 includes device 210, which corresponds to device 110 from FIG. 1, and pressure 260*a*, pressure 260*b*, pressure 260*c*, and pressure 260*d*, collectively referred to as pressures 260*a-d*. As illustrated in FIG. 2, device 210 can detect pressures 260*a-d*, where detected pressures 260*a-d* can be applied to any part of device 210 from any direction. Furthermore, each of pressures 260*a-d* may include a different amount of pressure. For example, pressure 260*a* may include a stronger pressure than pressure 260*b*. A pressure sensor in device 210, such as pressure sensor 115 in device 110 from FIG. 1, can thus sense and generate pressure data corresponding to each of pressures 260*a-d* being applied to device 210.

Figure 3:
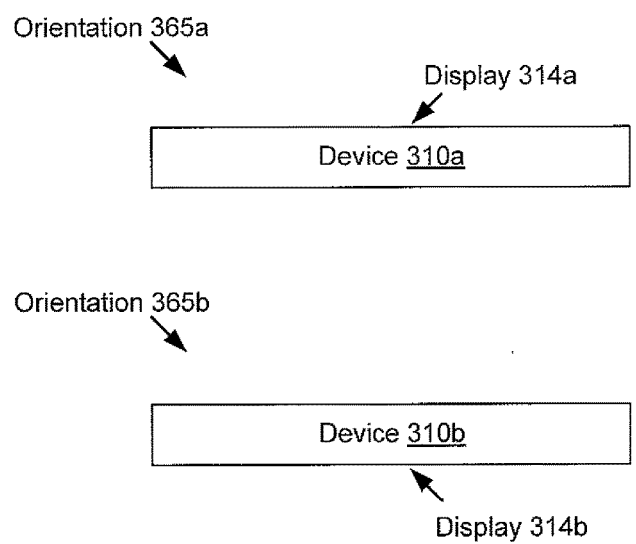
FIG. 3 presents an example of detecting an orientation of a device by using an orientation sensor, according to one implementation of the present disclosure.

FIG. 3 presents an example of detecting an orientation of a device by using an orientation sensor, according to one implementation of the present disclosure. FIG. 3 includes device 310*a* and device 310*b*, which both correspond to device 110 from FIG. 1, and display 314*a* and display 314*b*, which both correspond to display 114 from FIG. 1. FIG. 3 also includes orientation 165*a* and orientation 165*b*. As illustrated in FIG. 3, device 310*a* is oriented in an upward orientation with display 314*a* facing upwards. As also illustrated in FIG. 3, device 310*b* is oriented in a downward orientation with device 314*b* facing downwards. In each example orientation, an orientation sensor built into each of device 310*a* and device 310*b*, such as orientation sensor 116, is able to sense which orientation the device is being utilized in.

It should be noted that FIG. 3 only illustrates an upward orientation and a downward orientation for a device, however, the present disclosure is not limited to orientation sensors only senses upward and downward orientations. For example, orientation sensors can sense devices in any orientation, such as sideways or at some specific angle.

Figure 4:
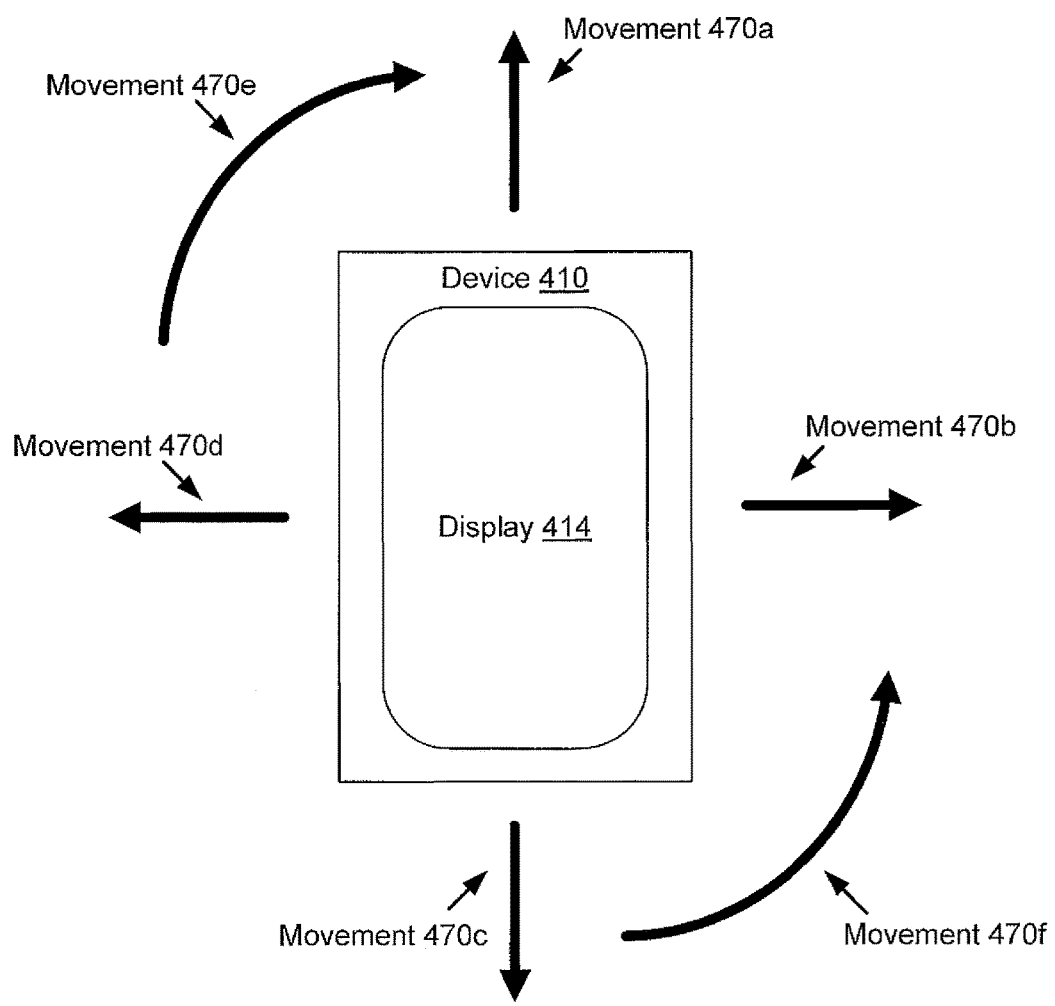
FIG. 4 presents an example of detecting movement of a device by using a motion sensor, according to one implementation of the present disclosure.

FIG. 4 presents an example of detecting movement of a device by using a motion sensor, according to one implementation of the present disclosure. FIG. 4 includes device 410 and display 414, which correspond respectively to device 110 and display 114 from FIG. 1. Also illustrated in FIG. 4 are movement 470*a*, movement 470*b*, movement 470*c*, movement 470*d*, movement 470*e*, and movement 470*f*, which are collectively referred to as movements 470*a-*

*f*. As illustrated in FIG. 4, a motion sensor in device 410, such as motion sensor 117 from FIG. 1, can sense a movement of device 410 in any direction, such as movements 410*a-f*. Furthermore, the motion sensor may sense how fast each of movements 470*a-f* are when being applied to device 410.

Figure 5:
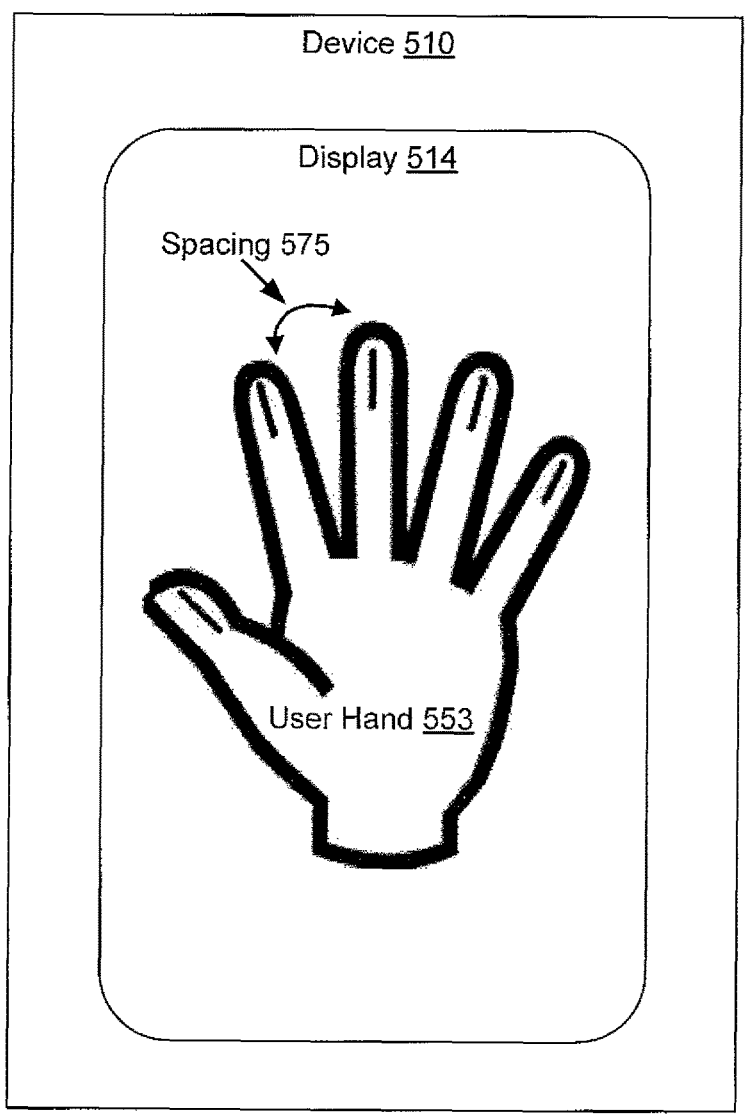
FIG. 5 presents an example of detecting dimensions of a user's hand placed on a device, according to one implementation of the present disclosure.

FIG. 5 presents an example of detecting dimensions of a user's hand placed on a device, according to one implementation of the present disclosure. FIG. 5 includes device 510 and display 514, which correspond respectively to device 110 and display 114 from FIG. 1. FIG. 5 further includes user hand 553 and spacing 575.

As illustrated in FIG. 5, a user may place his or her hand on display 514 of device 510, such as user hand 553. Device 510 may then use an interaction sensor built into display 514 to sense user hand 553 and collect data corresponding to user hand 553. After device 510 collects data corresponding to user hand 553, device 510 may then calculate the age and gender of the user of user hand 553. For example, and referring to FIG. 1, interaction sensor 130 may detect user hand 553 on display 114/514 and collect interaction data 129 corresponding to user hand 553. In such an example, interaction data 129 may include the size of user hand 553 and spacing 575, where spacing 575 corresponds to the spacing between the fingers of user hand 553. User identification 121 may then calculate user age 124 and user gender 125 based on interaction data 129 by comparing interaction data 129 to recorded interaction data 123, where recorded interaction data 123 includes data describing known measurements for hands based on the age and gender of users.

Figure 6:
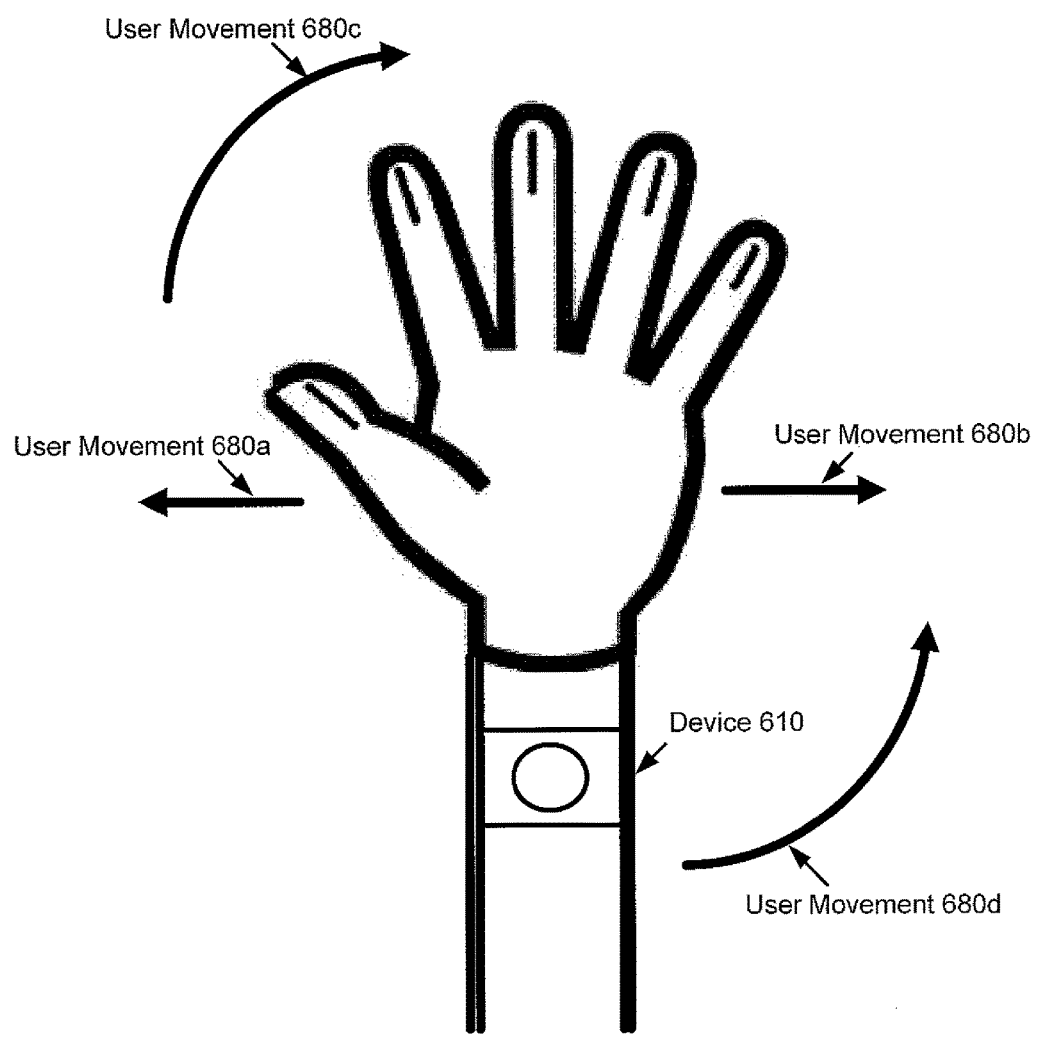
FIG. 6 illustrates an example of determining a user's age and a user's gender from a wearable device, according to one implementation of the present disclosure.

FIG. 6 illustrates an example of determining a user's age and a user's gender from a wearable device, according to one implementation of the present disclosure. FIG. 6 includes device 610, which corresponds to device 110 from FIG. 1. FIG. 6 further includes user movement 680*a*, user movement 680*b*, user movement 680*c*, and user movement 680*d*, collectively referred to as user movements 680*a-d*.

As illustrated in FIG. 6, device 610 now includes a wearable device, such as a watch. In the implementation of FIG. 6, device 610 is able to determine the age and gender of a user that is wearing device 610 based on user movements 680*a-d*, where user movements 680*a-d* include any movements that a user makes while wearing device 610. Device 610 determines the age and gender of the user be sensing and collecting data corresponding to user movements 680*a-d* using sensors, such as pressure sensor 115, orientation sensor 116, motion sensor 117, and interaction sensor 130 from FIG. 1, and calculating the age and gender of the user based on the user movement data using an algorithm, as discussed above.

It should be noted that in one implementation, device 610 may further include sensors that collect physical data corresponding to the heart rate of the user, the blood pressure of the user, the size of the wrist of the user, how fast the user walks, runs or moves body parts, or other physical data that can be sensed and collected about the user. Device 610 can then use the physical data of the user to calculate the age and gender of the user.

FIG. 7 shows a flowchart illustrating a method for real-time age profiling, according to one implementation of the present disclosure. The approach and technique indicated by flowchart 700 are sufficient to describe at least one implementation of the present disclosure, however, other implementations of the disclosure may utilize approaches and techniques different from those shown in flowchart 700. Furthermore, while flowchart 700 is described with respect to FIG. 1, the disclosed inventive concepts are not intended to be limited by specific features shown and described with respect to FIG. 1. Furthermore, with respect to the method illustrated in FIG. 7, it is noted that certain details and features have been left out of flowchart 700 in order not to obscure the discussion of inventive features in the present application.

Referring now to flowchart 700 of FIG. 7, flowchart 700 includes sensing, from at least one sensor, a user interaction from a user (710). For example, processor 111 of user device 110 may sense, using at least one of the sensors of device 110, user interaction 151 from user 150. As discussed above, device 110 includes at least four deferent sensors, which include pressure sensor 115, orientation sensor 116, motion sensor 117, and interaction sensor 130. User interaction 151 can include any interaction user 150 makes with device 110 while utilizing device 110. For example, user interaction 151 can include, but is not limited to, user 150 picking device 110 up, user 150 moving device 110, user 150 holding device 110, or user 150 utilizing the buttons and functions of device 110.

Flowchart 700 also includes receiving data corresponding to the user interaction with the at least one sensor (720). For example, processor 111 of device 110 may receive user interaction data 122 corresponding to user interaction 151 with at least one sensor of device 110. User interaction data 122 can include pressure data 126 corresponding to pressure data collected by pressure sensor 115, orientation data 127 corresponding to orientation data collected by orientation sensor 127, motion data 128 corresponding to motion data collected by motion sensor 117, and interaction data 129 corresponding to data collected by interaction sensor 130.

Flowchart 700 also includes determining an age of the user using the data corresponding to the user interaction (730). For example, processor 111 of device 110 may determine user age 124 of user 150 using user identification 121 based on user interaction data 122. As discussed above, user identification 121 calculates user age 124 by comparing user interaction data 122 with recorded interaction data 123, where recorded interaction data 123 includes data describing how users of device 110 are known to interact with device 110 based on their age.

Optionally, flowchart 700 also includes providing additional content to the user based on the age of the user (740). For example, processor 111 of device 110 may provide additional content to user 150 based on user age 124 of user 150. As discussed above, additional content can include, but is not limited to, advertisements, websites, and games.

From the above description it is manifest that various techniques can be used for implementing the concepts described in the present application without departing from the scope of those concepts. Moreover, while the concepts have been described with specific reference to certain implementations, a person of ordinary skill in the art would recognize that changes can be made in form and detail without departing from the scope of those concepts. As such, the described implementations are to be considered in all respects as illustrative and not restrictive. It should also be understood that the present application is not limited to the particular implementations described above, but many rearrangements, modifications, and substitutions are possible without departing from the scope of the present disclosure.

What is claimed is:

1. A device comprising:
   a motion sensor;
   an orientation sensor;
   a memory storing an algorithm; and a processor configured to execute the algorithm to:
  receive motion data from the motion sensor, the motion data describing movements of the device while the device is being used by a user interacting with the device;
  receive orientation data from the orientation sensor, wherein the orientation data include an orientation of the device while the device is being used by the user interacting with the device;
  weight the orientation data, using a first weight, based on recorded data;
  weight the motion data, using a second weight, based on the recorded data, the second weight being different than the first weight; and
  analyze the weighted orientation data and the weighted motion data describing the movements of the device to determine a calculated age range of the user;
  wherein the recorded data includes a first correlation between how users orient the device based on an age range, and a second correlation between how users move the device based on the age range.

2. The device of claim 1, wherein the device includes a pressure sensor, and wherein the processor is further configured to execute the algorithm to:
  receive pressure data from the pressure sensor, and wherein the pressure data include an amount of pressure applied to the pressure sensor by the user while the device is being used by the user interacting with the device;
  weight the pressure data; and
  analyze the weighted pressure data, the weighted orientation data and the weighted motion data to determine the calculated age range of the user.

3. The device of claim 2 further comprising a touch sensitive display, wherein the pressure sensor is a part of the touch sensitive display, and wherein the pressure data is obtained from the amount of pressure the user applies to the touch sensitive display.

4. The device of claim 3, wherein the processor is further configured to execute the algorithm to:
  determine a number of times the user touches the touch sensitive display within a predetermined time; and
  analyze the number of times, the weighted pressure data, the weighted orientation data and the weighted motion data to determine the calculated age range of the user.

5. The device of claim 1 further comprising a touch sensitive display, wherein the processor is further configured to execute the algorithm to:
  determine a shape of a hand of the user laid on the touch sensitive display, wherein determining the shape of the hand of the user includes determining a spacing between a plurality of fingers of the user.

6. The device of claim 5, wherein the processor is further configured to execute the algorithm to further:
  analyze the shape of the hand, the weighted orientation data and the weighted motion data to determine the calculated age range of the user.

7. The device of claim 1 further comprising a plurality of buttons, wherein the processor is further configured to execute the algorithm to:
  determine a number of the plurality of buttons the user presses within a predetermined time; and
  analyze the weighted motion data, the weighted orientation data and the number of the plurality of buttons the user presses within the predetermined time to determine the calculated age range of the user.

8. The device of claim 1 further comprising a plurality of buttons, wherein the processor is further configured to execute the algorithm to:
  determine how many of the plurality of buttons the user presses within a predetermined time; and
  analyze the weighted motion data, the weighted orientation data and how many of the plurality of buttons the user presses within the predetermined time to determine the calculated age range of the user.

9. A method for use by a device that includes a plurality of sensors comprising at least a motion sensor and an orientation sensor, the method comprising:
  receiving motion data from the motion sensor, the motion data describing movements of the device while the device is being used by a user interacting with the device;
  receiving orientation data from the orientation sensor, wherein the orientation data include an orientation of the device while the device is being used by the user interacting with the device;
  weighting the orientation data, using a first weight, based on recorded data;
  weighting the motion data, using a second weight, based on the recorded data, the second weight being different than the first weight; and
  analyzing the weighted orientation data and the weighted motion data describing the movements of the device to determine a calculated age range of the user;
  wherein the recorded data includes a first correlation between how users orient the device based on an age range, and a second correlation between how users move the device based on the age range.

10. The method of claim 9, wherein the device includes a pressure sensor, and wherein the method further comprises:
  receiving pressure data from the pressure sensor, and wherein the pressure data include an amount of pressure applied to the pressure sensor by the user while the device is being used by the user interacting with the device;
  weight the pressure data; and
  analyzing the weighted pressure data, the weighted orientation data and the weighted motion data to determine the calculated age range of the user.

11. The method of claim 10, wherein the pressure sensor is a part of a touch sensitive display, and wherein the pressure data is obtained from the amount of pressure the user applies to the touch sensitive display.

12. The method of claim 11, wherein the method further comprises:
  determining a number of times the user touches the touch sensitive display within a predetermined time; and
  analyzing the number of times, the weighted pressure data, the weighted orientation data and the weighted motion data to determine the calculated age range of the user.

13. The method of claim 9, wherein the device further includes a touch sensitive display, and wherein the method further comprises:
  determining a shape of a hand of the user laid on the touch sensitive display, wherein determining the shape of the hand of the user includes determining a spacing between a plurality of fingers of the user.

14. The method of claim 13, wherein the method further comprises:
  analyzing the shape of the hand, the weighted orientation data and the weighted motion data to determine the calculated age range of the user.

15. The method of claim 9, wherein the method further comprises:
- determining a number of the plurality of buttons the user presses within a predetermined time; and
- analyzing the weighted motion data, the weighted orientation data and the number of the plurality of buttons the user presses within the predetermined time to determine the calculated age range of the user.

16. The method of claim 9, wherein the method further comprises:
- determining how many of a plurality of buttons the user presses within a predetermined time; and
- analyzing the weighted motion data, the weighted orientation data and how many of the plurality of buttons the user presses within the predetermined time to determine the calculated age range of the user.

\* \* \* \* \*